United States Patent
Tuttle et al.

(10) Patent No.: US 10,532,332 B2
(45) Date of Patent: Jan. 14, 2020

(54) CONTINUOUS READY MIX JOINT TREATMENT AND TEXTURE PRODUCT PRODUCTION

(71) Applicant: UNITED STATES GYPSUM COMPANY, Chicago, IL (US)

(72) Inventors: Lori Tuttle, Orland Park, IL (US); Clinton Hattaway, Plano, TX (US); Erin Finley, Aurora, IL (US); Salvatore Immordino, Trevor, WI (US); Pamela Hargrove, Cary, IL (US)

(73) Assignee: UNITED STATES GYPSUM COMPANY, Chicago, IL (US)

( * ) Notice: Subject to any disclaimer, the term of this patent is extended or adjusted under 35 U.S.C. 154(b) by 0 days.

(21) Appl. No.: 15/486,918

(22) Filed: Apr. 13, 2017

(65) Prior Publication Data

US 2017/0326510 A1    Nov. 16, 2017

Related U.S. Application Data

(60) Provisional application No. 62/336,282, filed on May 13, 2016.

(51) Int. Cl.
   *B01F 3/00*    (2006.01)
   *B01F 3/14*    (2006.01)
   (Continued)

(52) U.S. Cl.
   CPC .............. *B01F 3/14* (2013.01); *A01N 61/00* (2013.01); *B01F 3/1221* (2013.01);
   (Continued)

(58) Field of Classification Search
   CPC ... C04B 40/0096; C04B 16/04; C04B 22/002; C04B 40/005; C04B 2111/00672;
   (Continued)

(56) References Cited

U.S. PATENT DOCUMENTS 5,573,333 A * 11/1996 Dahlman ............ B28B 17/0081
                                              366/141
6,193,408 B1 * 2/2001 Miura .................... B28C 5/0881
                                              366/304

(Continued)

FOREIGN PATENT DOCUMENTS

| EP | 2642024 A1 | 9/2013 |
| WO | 99/41002 A2 | 8/1999 |
| WO | 2015/176092 A2 | 11/2015 |

OTHER PUBLICATIONS

European Patent Office, International Search Report and the Written Opinion in International Application No. PCT/US2017/0351517 (dated Sep. 8, 2017).

*Primary Examiner* — Anshu Bhatia
(74) *Attorney, Agent, or Firm* — Leydig, Voit & Mayer, Ltd.; Philip T. Petti; Pradip K. Sahu

(57) ABSTRACT

A continuous ready mix joint or texture compound manufacturing system and a method for continuously manufacturing a ready mix joint or texture compound includes a continuous mixer having an inlet and an outlet, a pump disposed at the outlet of the continuous mixer, and a disperger having an inlet and an outlet. The continuous mixer is adapted to receive at least one dry ingredient and at least one wet ingredient at the inlet and continuously mix the at least one dry ingredient and the at least one wet ingredient to form a mixed composition. The pump is adapted to pump the mixed composition from the outlet of the continuous mixer to the inlet of the disperger. The disperger is adapted to receive the mixed composition and apply a shear force to the mixed composition to form a homogenized, disperged composition.

14 Claims, 3 Drawing Sheets

(51) Int. Cl.
  *A01N 61/00* (2006.01)
  *B01F 3/12* (2006.01)
  *B01F 5/06* (2006.01)
  *B01F 7/00* (2006.01)
  *B01F 13/10* (2006.01)
  *B01F 15/00* (2006.01)
  *B01F 15/02* (2006.01)
  *C04B 16/04* (2006.01)
  *C04B 22/00* (2006.01)
  *C04B 40/00* (2006.01)
  *C04B 111/00* (2006.01)
  *C04B 111/20* (2006.01)

(52) U.S. Cl.
  CPC .......... *B01F 3/1271* (2013.01); *B01F 5/0602* (2013.01); *B01F 7/0025* (2013.01); *B01F 7/0045* (2013.01); *B01F 7/00233* (2013.01); *B01F 13/103* (2013.01); *B01F 13/1027* (2013.01); *B01F 15/00142* (2013.01); *B01F 15/00162* (2013.01); *B01F 15/00175* (2013.01); *B01F 15/00246* (2013.01); *B01F 15/00422* (2013.01); *B01F 15/0283* (2013.01); *C04B 16/04* (2013.01); *C04B 22/002* (2013.01); *C04B 40/005* (2013.01); *C04B 40/0096* (2013.01); *B01F 2215/0047* (2013.01); *C04B 2111/00672* (2013.01); *C04B 2111/2092* (2013.01)

(58) Field of Classification Search
  CPC .. C04B 2111/2092; B01F 3/14; B01F 3/1221; B01F 3/1271; B01F 5/0602; B01F 7/00233; B01F 7/0025; B01F 7/0045; B01F 13/1027; B01F 13/103; B01F 15/00142; B01F 15/00162; B01F 15/00175; B01F 15/00246; B01F 15/00422; B01F 15/0283; B01F 2215/0047; A01N 61/00
  See application file for complete search history.

(56) References Cited

U.S. PATENT DOCUMENTS

| | | |
|---|---|---|
| 6,200,380 B1 | 3/2001 | Finkelstein et al. |
| 7,803,296 B2 * | 9/2010 | Miller ................... C04B 38/106 |
| | | 106/677 |
| 2005/0219938 A1 | 10/2005 | Rigaudon |
| 2007/0107860 A1 | 5/2007 | Doelle et al. |
| 2008/0303191 A1 | 12/2008 | Miller et al. |
| 2015/0051737 A1 | 2/2015 | Berman |

* cited by examiner

CONTINUOUS READY MIX JOINT TREATMENT AND TEXTURE PRODUCT PRODUCTION

CROSS REFERENCE TO RELATED APPLICATIONS

This application claims the benefit of U.S. Provisional Application No. 62/336,282, filed on May 13, 2016, the entirety of which is herein expressly incorporated by reference.

FIELD OF THE DISCLOSURE

The present disclosure generally relates to production of a family of liquiform construction materials and, more particularly, to a continuous production process for manufacturing the construction materials.

BACKGROUND

Interior walls of buildings are usually constructed using a number of wallboard panels such as gypsum boards or drywall. These boards are secured to frame members of the building using screws and/or nails, and are aligned adjacent to each other to form a wall surface. A number of products such as seam fillers and textures enable the achievement of a continuous wall surface that is suitable for finishing to the final customer's desired specifications. One such example is a composition commonly known as joint or ready mix compound is used to fill seams between adjacent panels and to conceal the fasteners to create a generally smooth wall surface free of interruptions, defects, and other imperfections. This compound is a generally smooth composition that can be easily applied in a number of layers and subsequently sanded to create a flat, uniform surface. A particular type of joint compound known as ready mix joint compound can reduce the preparation time required prior to beginning the process of applying the mixture to the wall surface by only requiring a brief mixing period to bring the material into uniformity. Conversely, traditional wall compound requires materials such as water to be added to a dry, bagged formula, which can take substantially more time to mix and prepare. Another example in this same family of products is a ready mix texturing compound that is also applied in the first stages of the wall building process to prepare the wall for its final form. For the purpose of clarity, these products will be referred to as ready mix compounds.

In existing systems and processes used to manufacture ready mix joint compound, bulk materials are shipped and stored at manufacturing facilities in large quantities. Batch processing is then utilized and generally includes mixing dry ingredients together in an operation such as a hopper or mixer, then combining the dry and wet ingredients in another separate mixer. The combined ingredients are then typically mixed to form a homogenous composition which is transferred into any number of holding tanks. This composition is then metered into desired packaging and/or holding containers for subsequent distribution. At each step of the manufacturing process, ingredients may need time to be sufficiently mixed before proceeding to subsequent steps. In some examples, it may be necessary to temporarily transport portions of the compound to a holding container prior to continuing the process. Upon producing a batch of compound, subsequent cycles can proceed to produce additional batches of blended material.

In these processes, quantities of bulk materials are fed into hopper systems in batches, which can result in substantial downtime when obtaining or storing additional materials. Each stage of the mixing process is time-consuming and can result in significant manufacturing downtime and/or delay. These manufacturing systems are oftentimes complex and physically sizable, thus requiring large and costly facilities having a high energy consumption. In current systems, one approach to overcoming production downtime involves using a number of separate process lines which operate in parallel such that one of the two or more processes is constantly in operation. Utilizing such a system may result in a "quasi-continuous" manufacturing process, but such a process necessitates additional manufacturing equipment and facility size. Further still, due to ingredient properties and/or quantities used to form the compound, individual batches of the compound may have varying compositions and thus may undesirably perform differently when used. These processes usually require an entire batch of the product to be completed prior to testing its properties.

SUMMARY

In accordance with one or more aspects, systems and approaches for continuous ready mix production may address a need for a low-cost, fast, and efficient manufacturing process. These systems can reduce and/or eliminate downtime typically associated with the time required to provide additional quantities of materials to be produced. Because most or all of the ingredients are simultaneously mixed together in a single mixing apparatus, overall cycle times are further reduced due to the elimination of the need to allow separate materials to be mixed into their corresponding compositions (e.g., separate wet and/or dry compositions). Additionally, these systems and approaches use less equipment than traditional manufacturing approaches and thus require less energy, physical space, and user skill and oversight to properly operate.

In some approaches, the system can be provided as a compact, portable device or devices usable at a remote construction location to provide a continuously available quantity of joint compound. As a result, time and costs associated with transporting separate batches of joint compound, readying the joint compound for use, and obtaining additional compound as needed are also reduced.

In accordance with a first exemplary aspect, a continuous joint compound production system may include a continuous mixer having an inlet and an outlet, a pump disposed at the outlet of the continuous mixer, and a disperger having an inlet and an outlet. The continuous mixer is adapted to receive at least one dry ingredient and at least one wet ingredient at the inlet and continuously mix the at least one dry ingredient and the at least one wet ingredient to form a mixed composition. The pump is adapted to pump the mixed composition from the outlet of the continuous mixer to the inlet of the disperger. The disperger is adapted to receive the mixed composition and apply a shear force to the mixed composition to form a homogenized, disperged composition.

In one form, a plurality of sensors may be disposed within the system. For example, a first sensor may be disposed at a location that allows a characteristic (such as a viscosity, a flow rate, a pressure, and/or a shear force) of the mixed composition to be measured and/or calculated. A second sensor may be disposed at a location that allows a similar characteristic to be measured or calculated. In these examples, the disperger is adapted to exert a force on the mixed composition such that the resulting viscosity of the disperged composition is less than that of the mixed composition. In one preferred approach, the mixed composition may have a viscosity between approximately 5,000 and 100,000 cP measured under typical process equipment and flow conditions of approximately 35 to 175 gallons per minute (gpm), and the disperged composition, upon exiting the disperger, may have a viscosity between approximately 5,000 and 100,000 cP measured under typical process equipment and flow conditions of approximately 35 to 175 gpm. Other examples are possible.

In some approaches, a feed rate of the at least one dry ingredient and/or the at least one wet ingredient is calculated and adjusted based on the post-disperger characteristics. As a result, joint compound uniformity is easily obtainable, which ensures the produced joint compound is manufactured according to consistent specifications. Any modifications to the ingredient composition can be made on the fly, thus requiring limited downtime to test the compound's properties. In some approaches, a controller can be used in conjunction with the sensors to conduct these comparisons and cause the feed rates to be modified.

In an exemplary approach, any number of dry and/or wet ingredients may be combined to form the joint compound. For example, solid ingredients can include any number of minerals, pigments, starches, thickeners, anti-microbials, and/or dyes. Liquid ingredients can include water, latex, defoamers, thickeners, and/or dispersants. Other examples are possible.

BRIEF DESCRIPTION OF THE DRAWINGS

The above needs are at least partially met through provision of the systems and approaches for ready mix production described in the following detailed description, particularly when studied in conjunction with the drawings, wherein.

Skilled artisans will appreciate that elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present invention. Also, common but well-understood elements that are useful or necessary in a commercially feasible embodiment are often not depicted in order to facilitate a less obstructed view of these various embodiments. It will further be appreciated that certain actions and/or steps may be described or depicted in a particular order of occurrence while those skilled in the art will understand that such specificity with respect to sequence is not actually required. It will also be understood that the terms and expressions used herein have the ordinary technical meaning as is accorded to such terms and expressions by persons skilled in the technical field as set forth above except where different specific meanings have otherwise been set forth herein.

DETAILED DESCRIPTION

Figure 1:
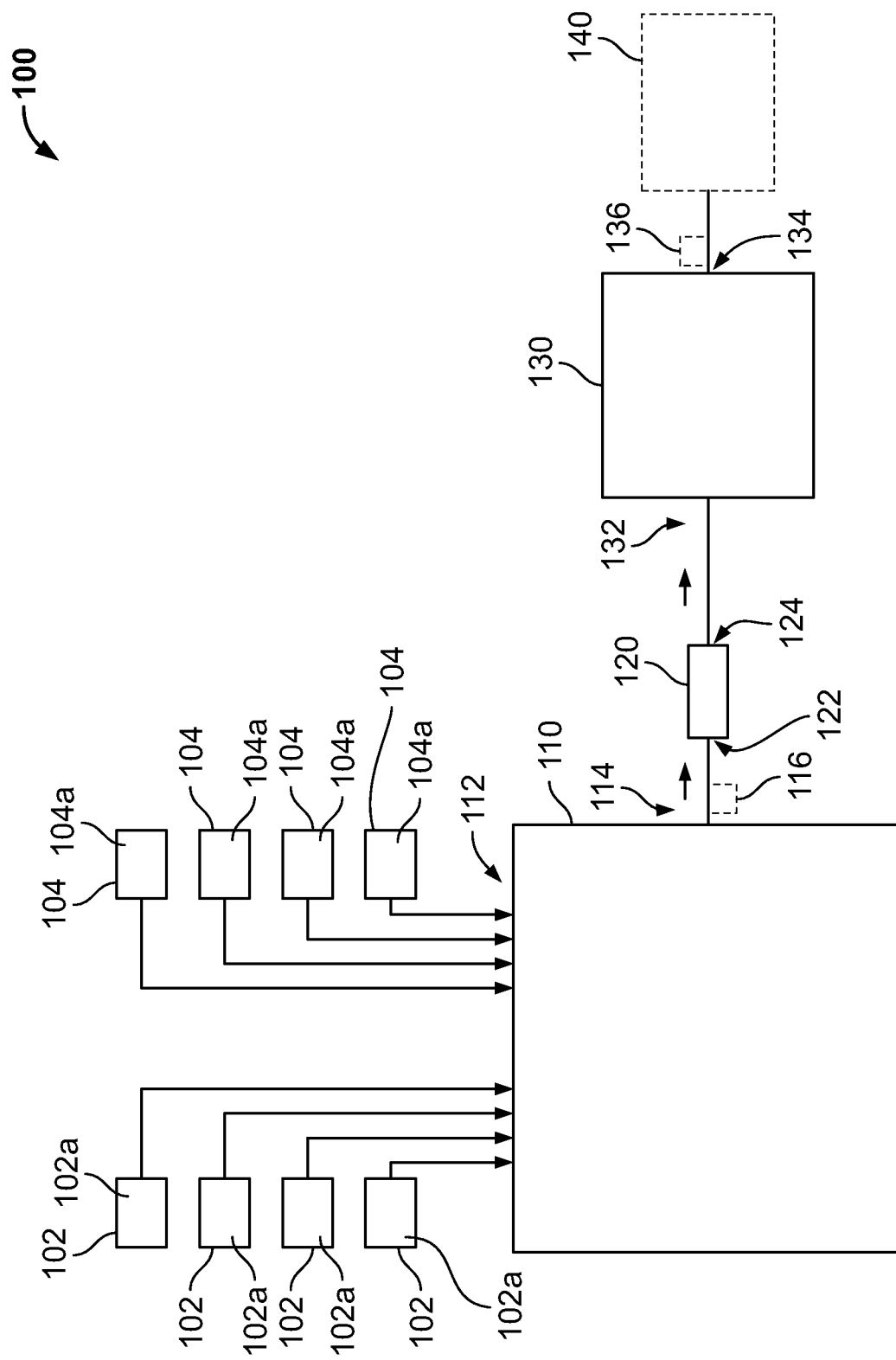
FIG. 1 comprises a block diagram of an exemplary continuous ready mix production system in accordance with various embodiments of the invention.

Generally speaking, pursuant to these various embodiments, a continuous ready mix joint compound production system is provided. As illustrated in FIG. 1, the system 100 includes any number of dry ingredient sources 102, any number of wet ingredient sources 104, a continuous mixer 110 having an inlet 112 and an outlet 114, a pump 120 having an inlet 122 and an outlet 124 and being disposed at the outlet 114 of the continuous mixer 110, and a disperger 130 having an inlet 132 and an outlet 134. The system 100 may include any number of additional components used in systems known to those having skill in the arts.

The continuous mixer 110 may be any type of mixer conventionally used to combine ingredients such as, for example, dry ingredients 102a from the dry ingredient sources 102 and the wet ingredients 104a from the wet ingredient sources 104, and may include any number of mixing apparatuses therein such as a number of paddles and/or blades to assist in mixing any materials added thereto. In other examples, the continuous mixer 110 may use any number of augers or rotating screws to incorporate and mix the materials. Other examples as well as combinations of these examples of mixing apparatuses are possible.

The continuous mixer 110 includes an inlet 112 for receiving the dry ingredient or ingredients 102a and the wet ingredient or ingredients 104a, an outlet 114 for transferring the ingredients therefrom, and a flow path extending between the inlet 112 and the outlet 114. Each dry and wet ingredient source 102, 104 includes an outlet in direct communication with the inlet 112 of the continuous mixer 110. The mixing apparatus contained in the continuous mixer 110 may be mounted in any number of configurations (such as, for example, horizontally or vertically) which are disposed in the flow path.

The continuous mixer is fed or supplied the dry and/or the wet ingredients 102a, 104a via any type of feeding system (not shown). For example, each of the dry and/or the wet ingredients 102a, 104a can be fed to the continuous mixer 110 via the sources 102, 104 that can include separate hoppers that guide the ingredients from a holding or storage tank to the continuous mixer 110. The feeding system can be metered to allow for accurate and precise continuous flow to the continuous mixer 110. The continuous mixer outlet 114 may have any dimension and/or configuration, and may be coupled to a tube, pipe, or other structure which can transport the material downstream.

In some examples, the dry ingredients 102 include any number of minerals, pigments, starches, thickeners, anti bacterials, dyes, and other commonly known materials. The wet ingredients 104 can include water, latex, defoamers, dispersants, as well as any other commonly known materials. It is understood that in some examples, a subset of materials may be separately fed to the system 100 after the mixed composition exits the outlet 114 of the continuous mixer 110. For example, a defoamer may be added to the mixed composition after the ingredients have been mixed together to form the mixed composition.

The inlet 122 of the pump 120 is disposed downstream of and in communication with the outlet 114 of the continuous mixer 110. The inlet 122 of the pump 120 is coupled to an opposing end of the tube or pipe. The pump 120 defines a fluid flow path from the inlet 122 to the outlet 124. In some examples, the pump 120 can be driven from a component of the continuous mixer 110 such as, for example, a central drive shaft in communication with a drive member of the pump 120. In other examples, the pump 120 can be separately driven by a motor or any other drive mechanism. Other examples are possible.

The disperger 130 may be any type of device adapted to generate a shear force and/or homogenize a material. The disperger 130 defines a flow path extending between the inlet 132 and the outlet 134. Further, the disperger 130 may have any number of rotatable paddles, disks, protrusions, and/or blades disposed on a central longitudinal axis and in the flow path which create a shearing effect in the material. These paddles may be disposed in any number of orientations relative to the flow path.

Figure 2:
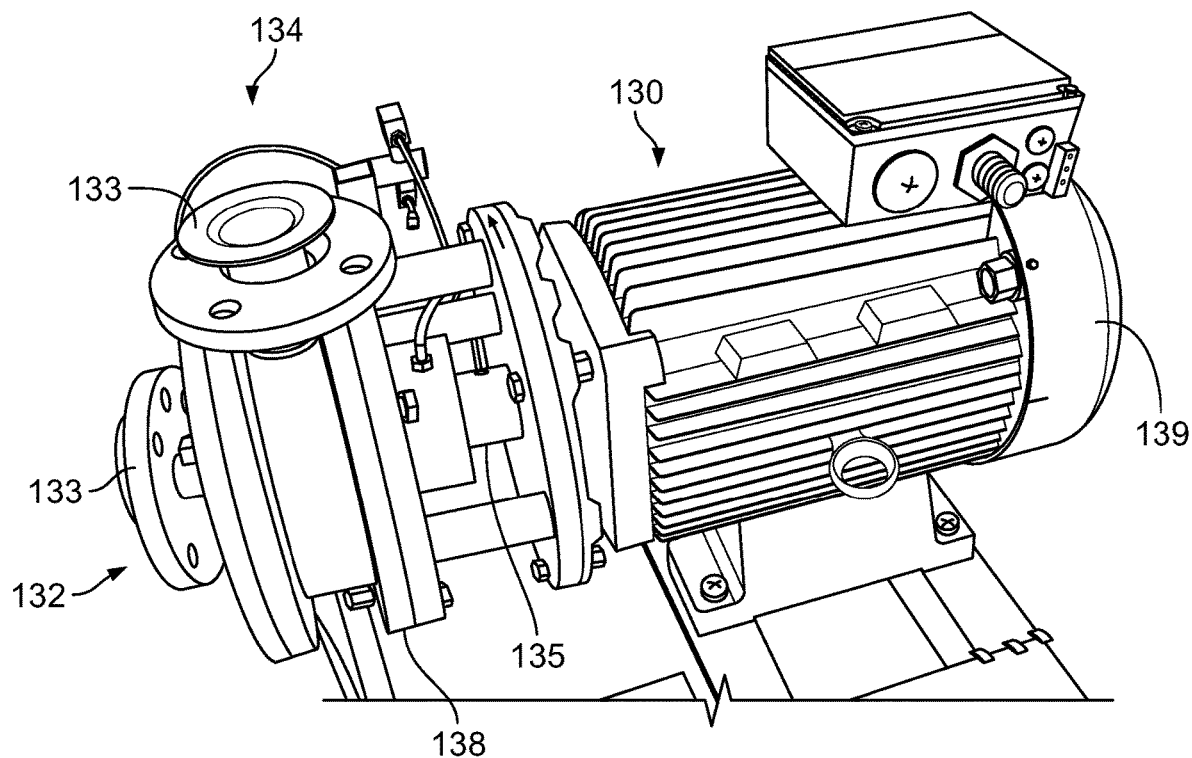
FIG. 2 comprises a perspective view of an exemplary disperger in accordance with various embodiments of the invention.
Figure 3:
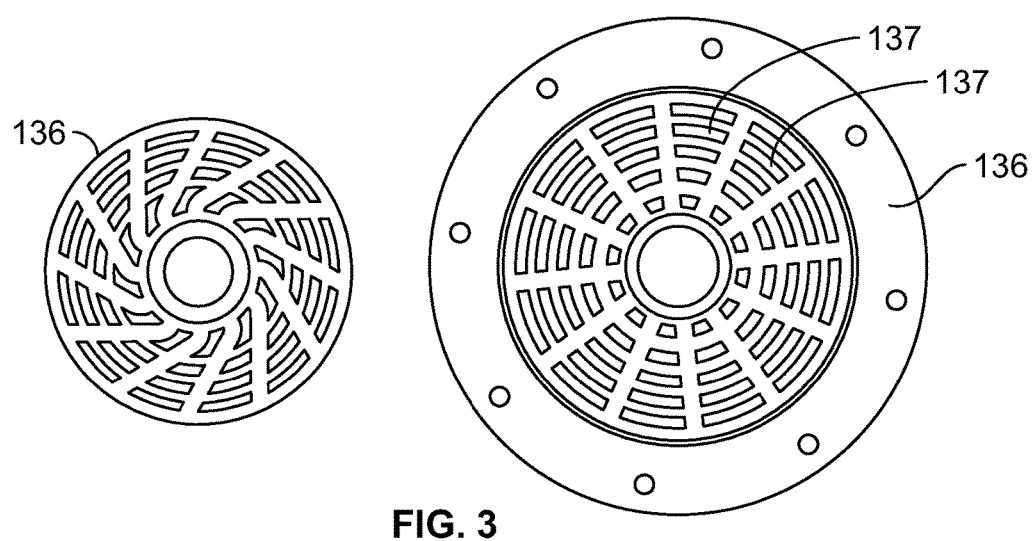
FIG. 3 comprises a front elevation view of an exemplary disperger disk in accordance with various embodiments of the invention.

In one version, the disperger 130 can include a Shear-Master disperger, manufactured by BVG, Inc. As illustrated in FIGS. 2 and 3, the inlet 132 and the outlet 134 of the disperger 130 include flanges 133 being appropriately dimensioned to couple to the piping in the system 100. The disperger 130 further includes any number of disperging disks 136 disposed in a disperging region 138 and a motor 139 capable of driving the disperging disk or disks 136. The motor 139 is coupled to the disperging region 138 via a number of cylindrical support members 131 and drives the disperging disks 136 via a drive shaft 135. The motor 139 can be any type of motor such as electric, hydraulic, fuel-burning, and the like.

The disperging disks 136 are generally cylindrical and include a central opening which accepts a drive shaft of the motor 139. The disperging disks 136 include a number of tabs or protrusions 137 arranged circumferentially about the opening which interact with the mixed composition. The disperging disks 136 rotate at high speeds to cause the mixed composition to homogenize and be disperged. Table 1 details a number of different disperger sizing alternatives, which could be implemented into the system 100 of the present application, and their corresponding specifications.

composition. In some examples, the continuous mixer 110 mixes the ingredients for between approximately 0.1 and 5.0 minutes and preferably between approximately 0.1 and 2.0 minutes as the ingredients 102a, 104a continuously move there through. In some forms, the mixed composition can have a viscosity between approximately 5,000 and 100,000 cP measured under typical process equipment and flow conditions of approximately 35 to 175 gpm. Other examples are possible.

The mixed composition then exits the continuous mixer 110 at the outlet 114 and enters the pump 120 at the inlet 122. A pumping force applied to the mixed composition causes it to traverse the flow path and exit the pump 120 at the exit 124. The mixed composition then enters the disperger 130 at the inlet 132, whereupon the disperger 130 exerts a shear mixing force on the mixed composition to cause it to homogenize and form a disperged material. The material may be disperged for a period of time such as, for example, between 0.1 and 1.0 seconds as it continuously moves through the disperger 130 before exiting the outlet 134. At this point, the disperged material can be either packaged or placed in one or more holding or storage tanks or containers 140 until needed. Upon exiting the disperger 130, some versions of the disperged material may begin to cure and increase in viscosity for approximately 24 hours as it becomes joint compound.

Upon exiting the continuous mixer 110, the mixed composition may have a viscosity of approximately 5,000 to 100,000 cP measured under typical process equipment and flow conditions of approximately 35 to 175 gpm. Similarly, upon exiting the disperger 130, the dispersed composition may have a viscosity of approximately 5,000 to 100,000 cP measured under typical process equipment and flow conditions of approximately 35 to 175 gpm. Thus, in some versions, the material worked on by the disperger 130 is considered to be shear-thinning (e.g., as having non-Newtonian characteristics). But, in other versions, the materials

TABLE 1

Disperger Models and Operating Properties

| Name | Power | | Flow Rate | | | | Flanges | |
|---|---|---|---|---|---|---|---|---|
| | KW | HP | m³/h | g/min | RPM | Solids % | Suction Side (inlet) | Pressure Side (outlet) |
| SM 15 | 15 | 20 | 5 | 22 | 3,000 | 65-78 | 40 1½" | 32 1¼" |
| SM 37 | 37 | 50 | 10 | 44 | 3,000 | 65-78 | 50 2" | 40 1½" |
| SM 55 | 55 | 75 | 15 | 66 | 3,000 | 65-78 | 65 2½" | 50 2" |
| SM 100 | 100 | 136 | 30 | 132 | 1,500 | 65-78 | 100 4" | 80 3" |
| SM 200 | 200 | 272 | 80 | 352 | 1,500 | 65-78 | 150 6" | 100 4" |

The disperger 130 described above can process solids up to 82% dissolved solids (d.s.) and can be used for the recovery of cleaning effluent. Additionally, neither a dispersing agent nor flush water is needed to operate the disperger 130. These dispergers can provide the highest rate of shear as well as plug flow shearing, meaning that material moves as a continuous unit through the system with no shearing between layers. Due to the compact nature of the disperger 130, minimal operating space is needed. Use of the disperger 130 may be fully automated, and can be monitored remotely. High production rates are possible, and online measurement of solids can further reduce production time.

In operation, the dry ingredient or ingredients 102a and the wet ingredient or ingredients 104a are fed to the continuous mixer 110 via the inlet 112. The continuous mixer 110 then mixes the ingredients 102a, 104a to form a mixed may not be shear-thinning. Generally speaking, the disperger 130 decreases the viscosity of the composition relative to the mixed composition. In some examples, the disperger 130 includes a disperging disk that rotates at a speed between approximately 1,000 to 4,000 rotations per minute, and may produce between approximately 50 to 200 horsepower.

The resulting joint compound can be a composition having between approximately 50-90% solids and the remaining volume being liquids. In one form, the composition consists of between 65-78% solids. Other examples are possible.

The foregoing system 100 can continuously produce joint compound at any desirable rate depending on the size and characteristics of the continuous mixer 110, the pump 120, and the disperger 130. As an example, the system 100 may have an overall flow rate of between approximately 25 to 200 gallons per minute, and in some versions between approximately 50 to 150 gallons per minute.

In some approaches, the system 100 can include any number of optional sensors 116, 136 which can measure any number of characteristics of the system 100. In one embodiment, the first optional sensor 116 is disposed at a location that is downstream of the outlet 114 of the continuous mixer 110 and upstream of the inlet 122 of the pump 120. Similarly, the second optional sensor 136 can be disposed at a location that is downstream of the outlet 134 of the disperger 130. The optional sensors 116, 136 can operate by being physically contacted by the mixture flowing through the piping and/or tubing. For example, the piping and/or tubing may have openings in which the optional sensors 116, 136 can be inserted into while still minimizing interruption to the flow of the material. Other examples of coupling and/or operating the optional sensors 116, 136 are possible.

In one form, the optional sensors 116, 136 can be flow rate meters to control the throughput of the process. In other forms, the optional sensors 116, 136 can include any other type of sensors such as, for example, flow rate sensors, pressure gauges, strain gauges, temperature sensors, and the like which can measure any number of characteristics of the ingredients, mixed composition, and/or the dispersed composition. Other examples are possible. Further, any number of different types of sensors and/or additional sensors can be disposed at various locations within the system 100 as desired.

The system 100 may also include a controller (not shown) communicatively coupled to any number of components thereof using any known wired and/or wireless communication protocol. The controller may be any type of electronic processing device capable of performing calculations and/or executing tasks. It is understood that the controller may include any number of processors, inputs, transitory and non-transitory memory modules, displays, outputs, and any additional components as desired.

In a first example, the data obtained from the optional sensors 116, 136 are transmitted to the controller and displayed to a user. This information may be useful in determining whether material characteristics (e.g., a composition's flow rate) fall within a desired and/or ideal range. In the event that one of the characteristics falls outside of the desired range, the controller can notify the user to take necessary corrective action to consistently maintain a desired property of the completed product. In another example, the controller may further be coupled to any number of components capable of adjusting operating parameters of the system 100. For example, the controller 100 may be a feedback controller adapted to receive or calculate a difference between estimated and measured sensor values and adjust parameters (such as, for example a feed rate) of any of the dry ingredients 102*a* and/or wet ingredients 104*a*. The controller may also be adapted to adjust an operating speed of the continuous mixer 110, the pump 120, or the disperger 130. Other examples are possible.

In an embodiment, the system 100 can include an optional static mixer (not shown) disposed between the outlet 114 of the continuous mixer 110 and the inlet 132 of the disperger 130. The static mixer can be provided to further improve the mixing of the mixed composition prior to entering the disperger 130. In one version, the static mixer can be downstream of the pump 120 and upstream of the disperger 130. In another version, the static mixer can be downstream of the continuous mixer 110 and upstream of the pump 120.

The static mixer can define a flow channel extending between an inlet and an outlet, and can include a stationary mixing device disposed in the flow channel. In one embodiment, the static mixer is disposed downstream of the pump 120 and accordingly can utilize forces generated thereby to propel the mixed composition through the flow channel. The stationary mixing device may be any type of device or devices such as, for example, plates, helixes, baffles, and the like which, when the mixed composition moves across, cause the mixed composition to continue mixing. By providing a more thoroughly mixed composition, the disperger may not need to exert as much energy to operate.

Figure 4:
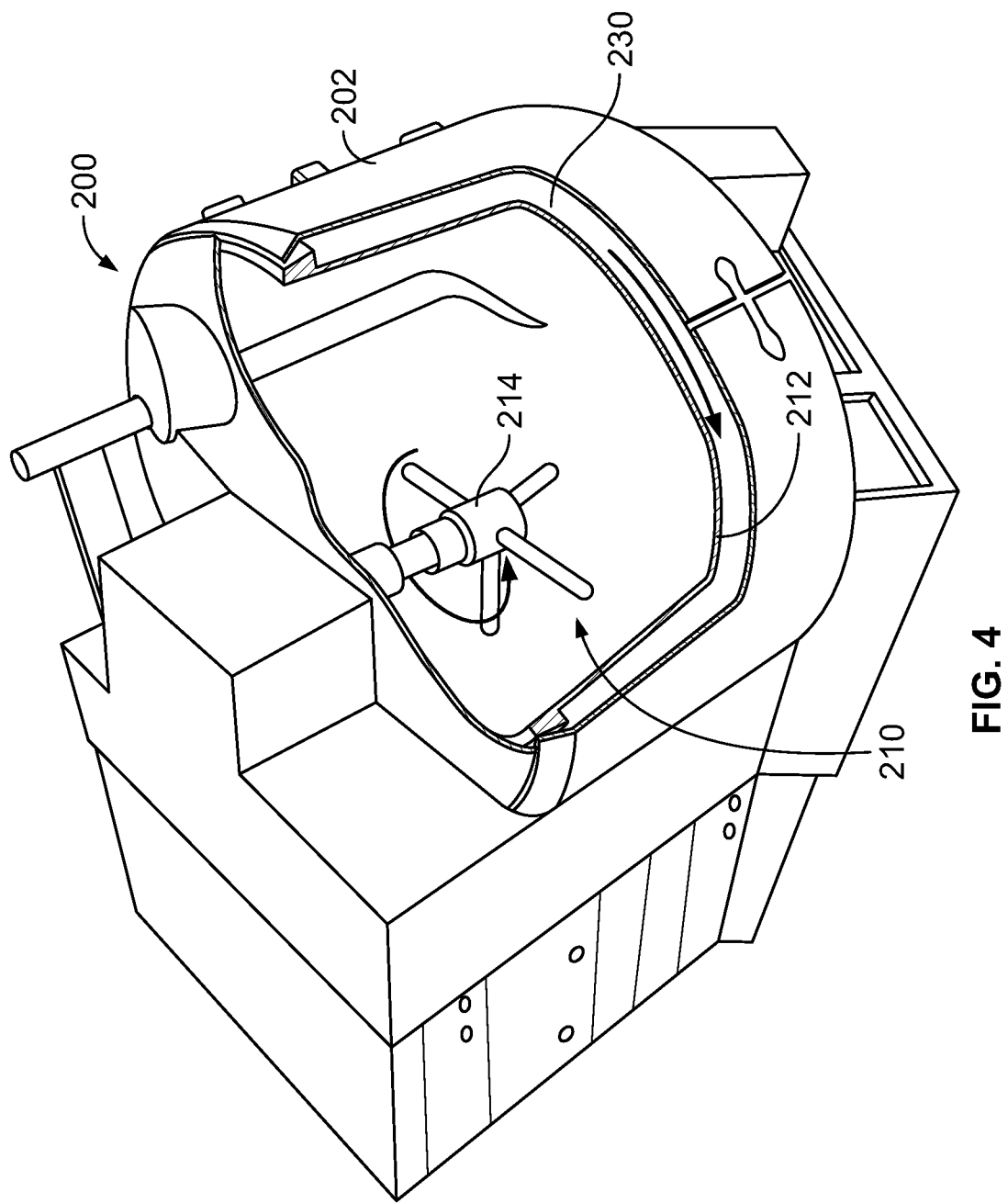
FIG. 4 comprises a perspective view of an alternate continuous ready mix production system wherein a continuous mixer is integrated into a single unit with a disperger in accordance with various embodiments of the invention.

Turning to FIG. 4, in some examples, an alternative system 200 includes similar components as the system 100 of FIGS. 1-3 such as a continuous mixer 210 and a disperger 230. However, in this system 200, the continuous mixer 210 and the disperger 230 are integrated into a single housing 202. In one example, the system 200 can be a Continuous Mixer manufactured by Maschinenfabrik Gustav Eirich GbmH & Co. Other examples are possible.

In these examples, the mixer 210 includes a drum 212 that receives the dry ingredient or ingredients and the wet ingredient or ingredients. The drum can be positioned in any number of orientations such as, for example, generally horizontal, vertical, or at any desired angle therebetween. The mixer 210 also includes a mixing device 214, which, in some configurations, can be a paddle, auger, or other rotating device. In some examples, both the drum 212 and the mixing device 214 can rotate to mix the wet and dry ingredients.

The disperger 230 is disposed about a perimeter of the housing 202 and operates in a similar manner as the disperger 130 of FIGS. 1-3. Upon the ingredients being adequately mixed, the ingredients are then moved to the disperger 230, which generates a shear force on and/or homogenizes the mixture. In some examples, the housing 202 may include a flow path that causes the mixed ingredients to flow to the disperger 230. The flow path may include a door or other device that remains closed while the ingredients are mixing, then subsequently opens to allow the mixed ingredients to be dispersed. The housing 202 can also include a scraper or other device to assist removing the material to subsequent locations (e.g., to storage tanks or containers).

So configured, the mixing and dispersing process can be less time-consuming than with traditional systems. These systems may also operate at higher mixing speeds which can in turn require less total energy. Such a system does not require the use of a pump to transport the mixed ingredients from the mixer 210 to the disperger 230, thus reducing components and costs. Additionally, a unitary system 200 can provide for more effective mixing by optimizing raw materials, and can be easy to maintain.

So configured, systems and approaches for continuously producing a ready mix joint compound require minimal down time and operating power. As a result of the reduced down time, overall cycle times are reduced, thus allowing additional joint compound to be produced, which in turn can reduce overall job times. Due to the lack of numerous apparatuses and components, less energy is required to execute the process, and the size of the manufacturing facilities can be scaled down. In the event that existing facilities are used, multiple systems can be installed in the facility to correspondingly multiply output. By optimizing individual system components and by providing automated feedback control, the resulting joint compound may have uniform and consistent material characteristics.

Those skilled in the art will recognize that a wide variety of modifications, alterations, and combinations can be made with respect to the above described embodiments without departing from the scope of the invention, and that such modifications, alterations, and combinations are to be viewed as being within the ambit of the inventive concept.

What is claimed is:

1. A method of continuously manufacturing a joint compound product, the method comprising:
    feeding joint compound ingredients comprising at least one dry ingredient and at least one wet ingredient to a continuous mixing apparatus;
    continuously mixing the joint compound ingredients using the continuous mixing apparatus to form a mixed joint compound composition;
    transporting the mixing joint compound composition in the disperger by applying a shear force via a dispersing disk rotating at a speed of at least 1,000 revolutions per minute to form a dispersed joint compound composition wherein the mixed joint compound composition is transported into the disperger by applying a pumping force to the mixed joint compound composition via a pump interposed between the continuous mixer and the disperger.

2. The method of claim 1, further comprising:
    calculating, using a first sensor, a pre-disperger characteristic, of the mixed joint compound composition before entering the disperger; and
    calculating, using a second sensor, a post-disperger characteristic of the dispersed joint compound composition.

3. The method of claim 2, wherein the pre-disperger characteristic and the post-disperger characteristic comprises at least one of:
    (a) a viscosity value;
    (b) a flow rate value;
    (c) a pressure value;
    (d) a temperature value;
    (e) a shear force; and
    (f) a content of solids.

4. The method of claim 1, further comprising:
    calculating a feed rate of at least one of the joint compound ingredients; and
    adjusting the feed rate of said at least one of the joint compound ingredient based on the viscosity of the dispersed joint compound composition.

5. The method of claim 1, wherein the mixed joint compound composition has a viscosity between approximately 5,000 and 100,0000 cP measured at approximately 35 to 175 gallons per minute.

6. The method of claim 1, wherein the dispersing disk is rotating at a rate of between approximately 1,000 and 4,000 revolutions per minute.

7. The method of claim 1, further comprising transporting the dispersed joint compound composition to a holding tank for packaging.

8. The method of claim 1, further comprising mixing, via a static mixer, the mixed joint compound composition after leaving the continuous mixing apparatus and prior to entering the disperger.

9. The method of claim 1, wherein the at least one dry ingredient comprises at least one of:
    (a) a mineral;
    (b) a pigment;
    (c) a starch
    (d) a thickener;
    (e) as anti-bacterial; and
    (f) a dye.

10. The method of claim 1, wherein the at least one wet ingredient comprises at least one of:
    (a) water;
    (b) latex;
    (c) a defoamer;
    (d) a thickener
    (e) a dispersant; and
    (f) an anti-microbial additive.

11. The method of claim 1, Wherein the mixed joint compound composition is dispersed in the disperger such that a viscosity of the mixed joint compound composition before entering the disperger is greater than the viscosity of the disperger joint compound composition.

12. The method of claim 1, further comprising:
    sensing a first value of a characteristic of the mixed joint compound composition prior to entering the disperger;
    sensing a second value of the Characteristic of the dispersed joint compound composition; and
    adjusting a feed rate of at least one of the joint compound ingredients based on comparing the second value and the first value of the characteristic of the dispersed joint compound composition and the mixed joint compound composition, respectively.

13. The method of claim 5, wherein the dispersed joint compound composition has a viscosity that is less than the viscosity of the mixed joint compound composition.

14. The method of claim 9, wherein the at least one wet ingredient comprises at least one of:
    (i) water;
    (ii) latex;
    (iii) a defoamer;
    (iv) a thickener;
    (v) a dispersant; and
    (vi) an anti-microbial additive.

* * * * *

UNITED STATES PATENT AND TRADEMARK OFFICE
CERTIFICATE OF CORRECTION

PATENT NO.        : 10,532,332 B2
APPLICATION NO.   : 15/486918
DATED             : January 14, 2020
INVENTOR(S)       : Tuttle et al.

It is certified that error appears in the above-identified patent and that said Letters Patent is hereby corrected as shown below:

In the Claims

Column 9, Claim 1, Line 16-17:
"transporting the mixing joint compound composition in the disperger" should be replaced with "transporting the mixing joint compound composition into a disperger"

Column 10, Claim 11, Line 25:
"Wherein" should be replaced with "wherein"

Column 10, Claim 12, Line 33:
"Characteristic" should be replaced with "characteristic"

Signed and Sealed this
Tenth Day of November, 2020

Andrei Iancu
*Director of the United States Patent and Trademark Office*